(12) United States Patent
Madhuri Sugathan et al.

(10) Patent No.: US 11,484,650 B2
(45) Date of Patent: Nov. 1, 2022

(54) INFUSION CONTROL DEVICES FOR MONITORING AND SETTING RATES OF INFUSION

(71) Applicants: Vishnu Madhuri Sugathan, Kollam (IN); Sanjai Raj Rajendran, Ernakulam (IN)

(72) Inventors: Vishnu Madhuri Sugathan, Kollam (IN); Sanjai Raj Rajendran, Ernakulam (IN)

(73) Assignee: EVELABS TECHNOLOGIES PRIVATE LIMITED, Kollam (IN)

( * ) Notice: Subject to any disclaimer, the term of this patent is extended or adjusted under 35 U.S.C. 154(b) by 194 days.

(21) Appl. No.: 16/962,530

(22) PCT Filed: Jan. 17, 2019

(86) PCT No.: PCT/IB2019/050386
§ 371 (c)(1),
(2) Date: Jul. 16, 2020

(87) PCT Pub. No.: WO2019/142125
PCT Pub. Date: Jul. 25, 2019

(65) Prior Publication Data
US 2021/0085860 A1    Mar. 25, 2021

(30) Foreign Application Priority Data
Jan. 17, 2018   (IN) .............................. 201841001942

(51) Int. Cl.
*A61M 5/168*   (2006.01)
*A61M 5/14*    (2006.01)

(52) U.S. Cl.
CPC ...... *A61M 5/16886* (2013.01); *A61M 5/1411* (2013.01); *A61M 5/16877* (2013.01); *A61M 2205/18* (2013.01); *A61M 2205/3327* (2013.01)

(58) Field of Classification Search
CPC ............ A61M 5/16886; A61M 5/1411; A61M 5/16877; A61M 2205/18; A61M 2205/3327
USPC .......................................................... 604/65
See application file for complete search history.

(56) References Cited

U.S. PATENT DOCUMENTS

2018/0177942 A1* 6/2018 Hirata ................ A61M 39/281

* cited by examiner

*Primary Examiner* — Phillip A Gray
(74) *Attorney, Agent, or Firm* — Evelabs Technologies Private Limited (57) ABSTRACT

The device comprises of a housing defining a channel there through, a torsion-spring based clamping mechanism, a drop sensor connected with circuitry, a manual infusion fluid regulation mechanism and a power source. An upper portion of the channel accommodates at least a part of a drip chamber and a lower portion of the channel accommodates at least a part of infusion tubing. The clamping mechanism comprises of one or more torsion springs and is configured for engaging and holding drip chamber and can be adjusted according to the drip chamber diameter. The drop sensor and the circuits coupled with it are configured for detecting real time drop rate of the infusion fluid. The regulation mechanism comprises of a drivable pinching element for sliding into the channel and compressing the infusion tubing thereby regulating the flow of the infusion fluid through the infusion tubing.

11 Claims, 9 Drawing Sheets

INFUSION CONTROL DEVICES FOR MONITORING AND SETTING RATES OF INFUSION

TECHNICAL FIELD

The present disclosure generally relates to the field of medical devices. More particularly, the present disclosure relates to devices for monitoring and setting the flow of infusion fluid in infusion systems.

BACKGROUND

Infusion treatments done with infusion devices are not affordable as a common practice and most health practitioners tend to resort to gravity flow infusion methods. Gravity-drip infusion methods are less accurate and require frequent monitoring for delivering fluids at the prescribed rate.

Usually the flow rates in gravity fed infusions are controlled with a roller clamp that comes along with the infusion set. It requires a big effort from the user side to set flow at a prescribed level and precision of flow rate is not possible with a roller clamp as there is a tendency towards flow rate variation. Flow rate variation also occurs immediately after setting the rate as the user takes the hands off the roller clamp, since the roller clamp is a slide up-down mechanism which works due to direct pressure from hand. The flow rate in a gravity infusion varies throughout the course based on several other factors as well-patient's blood pressure, head variation in the IV bag, kink in IV tube etc. If such changes go unnoticed, the patient tends to develop critical health conditions due to over dosage or under dosage. Further, the creep/cold flow property and the hysteresis properties of the deformable infusion tubing add to the woes.

Conventional infusion monitors that are available in the market are costlier and some models produce continuous alarms right in front of the patients, causing a bad patient experience.

In the light of aforementioned discussion, there exists a need for infusion control devices in which the infusion flow rate can be set and controlled with high levels of precision and are yet affordable. Also, it would be preferable if such infusion control devices could be attached to the drip chambers with ease and could accommodate different sized drip chambers. The present invention discloses affordable infusion control devices that can monitor, set and control the real time drop rate with a higher precision. The infusion control device has a drop sensor connected with circuits for detecting real time drop rate, a torsion-spring based clamping mechanism for holding drip chambers of different diameters and a manual gear-based flow regulating mechanism for regulating the flow of infusion fluid through the infusion tubing. The flow regulating mechanism of the disclosed device is configured in such a manner to minimise the effects of creep and hysteresis.

With reference to drop rate sensors, when drip chambers of different diameters are used, because of differences in the line of flow there are bound to be difficulties in optimal sensing. Also, any unwanted movements (during ambulance travel, movement of patient's hand etc.) can cause the drip chambers to move further leading to suboptimal sensing of the drop rate. The infusion control device disclosed in the present invention solves the above identified problem by providing a parallel array of sensors that can detect the line of flow of drops in different sized drip chambers. Further, the clamping mechanism provided herein along with the parallel array of sensors keeps the line of fluid flow within the angle of view of the sensors during any unwanted movement.

BRIEF SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

Exemplary embodiments of the present disclosure are directed towards infusion control devices for monitoring and setting the flow of an infusion fluid in an infusion system. The device comprises of a housing defining a channel there through, a torsion-spring based clamping mechanism, a drop sensor connected with circuitry, a manual infusion fluid regulation mechanism and a power source. An upper portion of the channel is configured for accommodating at least a part of a drip chamber and a lower portion of the channel is configured for accommodating at least a part of infusion tubing. The clamping mechanism comprises of one or more torsion springs and is configured for engaging and holding a drip chamber within the upper portion and to be adjusted according to the diameter of the drip chamber. The drop sensor detects the drops falling through the drip chamber and is disposed in the upper portion adjacent to the drip chamber. The circuits coupled with the drop sensor are disposed substantially within the housing and are configured for processing the information received from the sensor for detecting real time drop rate of the infusion fluid. The regulation mechanism is disposed substantially within the housing and comprises of a drivable pinching element for sliding into the channel and compressing the infusion tubing thereby regulating the flow of the infusion fluid through the infusion tubing. The power source is disposed within the housing and is configured for powering the drop sensor and the circuits.

Other exemplary embodiments of the present subject matter are directed towards clamping mechanisms for infusion devices for accommodating drip chambers. The mechanism comprises of one or more of torsion springs that are disposed in the upper portion. The spring coils of the torsion springs ends in a tangentially extending first leg that is bent and configured for engaging and holding the drip chamber within the upper portion and further being configured to be adjusted according to the diameter of the drip chamber.

Other exemplary embodiments of the present subject matter are directed towards manual infusion fluid regulation mechanisms for infusion devices. The mechanism comprises of a rotary drive, a first gear with a first axle with one end of the first axle being connected with the drive. The first gear is enmeshed with a second gear having a hollow axle. A drivable pinching element comprising a threaded shaft with a stopper at one end is substantially housed within the hollow axle and is configured for sliding into the channel and compressing the infusion tubing thereby regulating the flow of the infusion fluid through the infusion tubing. When the rotary drive is driven manually, the first axle rotates thereby causing rotation of the first and the second gears leading to the linear movement of the pinching element, whereby the stopper compresses the infusion tubing.

It is an object of the present invention to disclose infusion control devices that are affordable, portable and non-invasive.

It is another object of the present invention to disclose infusion control devices that can accommodate diffusion chambers with different diameters and that can be easily clamped to the drip chamber.

It is another object of the present invention to disclose infusion control devices that have an improved drop sensing mechanism.

It is another object of the present invention to disclose infusion control devices that have a flow regulating mechanism with minimum effects of creep and hysteresis.

BRIEF DESCRIPTION OF DRAWINGS

Other objects and advantages of the present invention will become apparent to those skilled in the art upon reading the following detailed description of the preferred embodiments, in conjunction with the accompanying drawings, wherein like reference numerals have been used to designate like elements, and wherein:

FIGS. 5A to 6B are schematic representations of different views of the infusion control device that depict the variation in the position of the torsion spring legs corresponding to the diameter of the drip chamber.

DETAILED DESCRIPTION

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting.

The use of "including", "comprising" or "having" and variations thereof herein is meant to encompass the items listed thereafter and equivalents thereof as well as additional items. The terms "a" and "an" herein do not denote a limitation of quantity, but rather denote the presence of at least one of the referenced item. Further, the use of terms "first", "second", and "third", and the like, herein do not denote any order, quantity, or importance, but rather are used to distinguish one element from another.

According to different non limiting exemplary embodiments of the present disclosure, infusion control devices for monitoring and setting the flow of an infusion fluid in an infusion system are disclosed.

In accordance with different non limiting exemplary embodiments of the present subject matter, clamping mechanisms for infusion devices for accommodating different sized drip chambers are disclosed.

According to different non limiting exemplary embodiments of the present disclosure, manual infusion fluid regulation mechanisms for infusion devices are disclosed.

Referring to FIGS. 1-8D, they depict infusion control devices 100 that comprise of a housing 102 defining a channel 104 there through, a torsion-spring 106 based clamping mechanism, a drop sensor connected with a circuitry 128, a manual infusion fluid regulation mechanism and a power source. An upper portion 108 of the channel 104 is configured for accommodating at least a part of a drip chamber 114 and a lower portion 110 of the channel 104 is configured for accommodating at least a part of infusion tubing 116.

The clamping mechanism comprises of two torsion springs 106 and is configured for engaging and holding a drip chamber 114 within the upper portion 108 and to be adjusted according to the diameter of the drip chamber 114. The drop sensor detects the drops 122 falling through the drip chamber and is disposed in the upper portion 108 adjacent to the drip chamber 114. The circuits coupled with the drop sensor are disposed substantially within the housing 102 and are configured for processing the information received from the sensor for detecting real time drop rate of the infusion fluid. The regulation mechanism is disposed substantially within the housing 102 and comprises of a drivable pinching element for sliding into the channel 104 and compressing the infusion tubing 116 thereby regulating the flow of the infusion fluid through the infusion tubing 116. The power source is disposed within the housing 102 and is configured for powering the drop sensor and the circuits.

Figure 1:
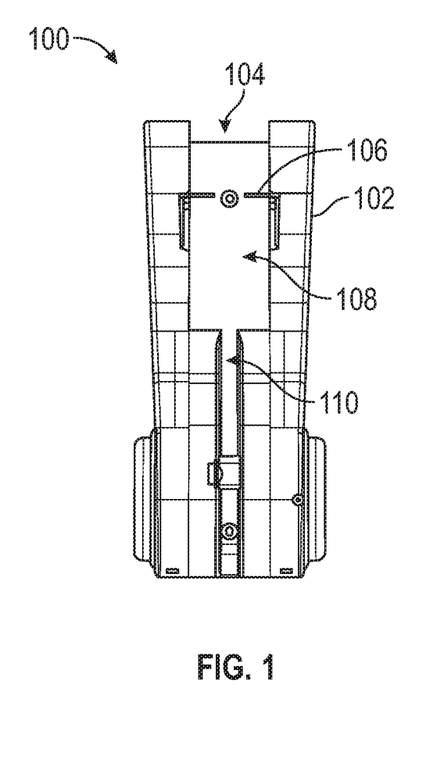
FIG. 1 is a schematic representation of a rear view of an infusion control device, in accordance with a non limiting exemplary embodiment of the present disclosure.
Figure 2:
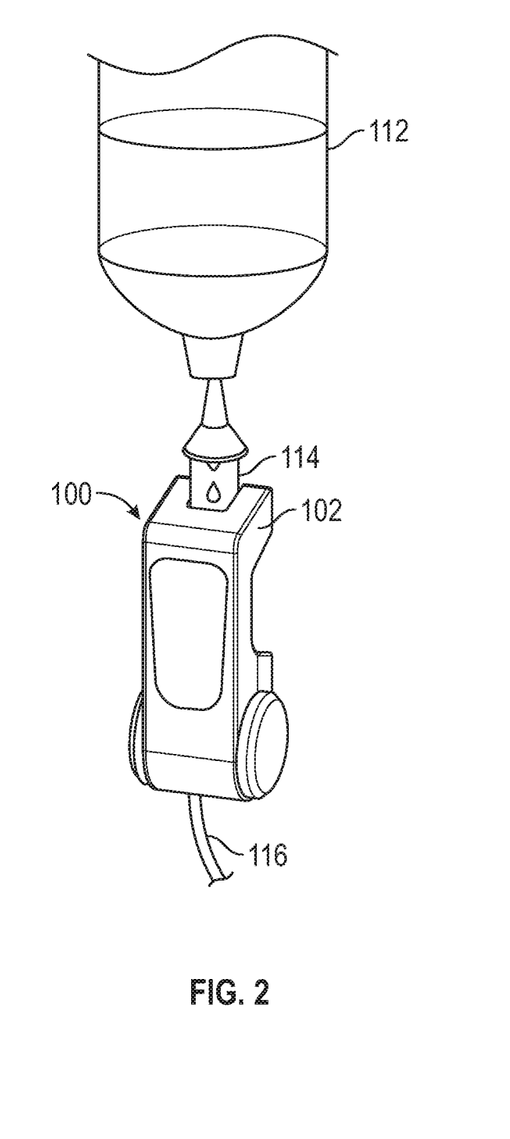
FIG. 2 is a schematic representation of an isometric view of the infusion control device shown in FIG. 1 being clamped to an infusion system. Clamping mechanism not shown for purposes of clarity.

Referring specifically to FIG. 2, it shows the device 100 in a clamped position with the drip chamber 114 of the infusion system. The infusion system typically has a container 112 filled with infusion fluid that is hung on a support, whereby drops of infusion fluid drips into a drip chamber 114 and then flows through an infusion tubing 116 to an injection needle for injection into a patient.

Figure 3:
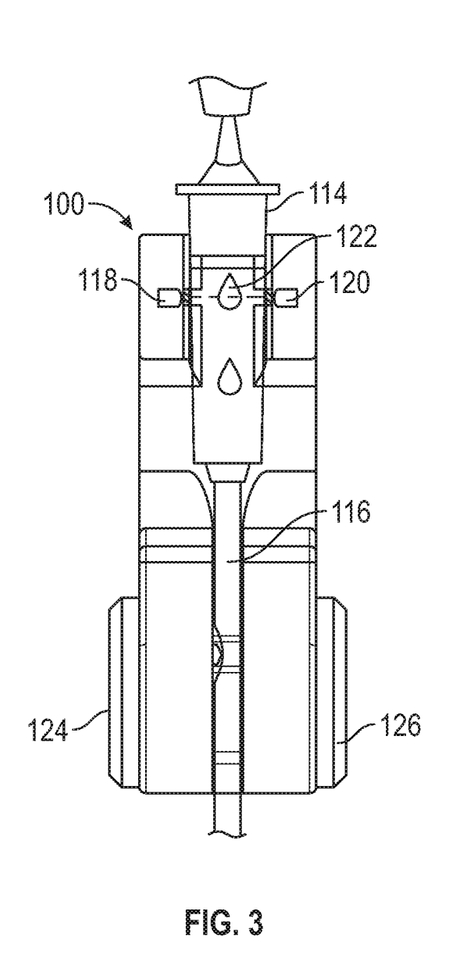
FIG. 3 is a schematic representation of a rear view of the infusion control device shown in FIG. 2. Clamping mechanism not shown for purposes of clarity.

Referring specifically to FIG. 3, the mechanical dial 124 on a first side of the device 100 is used for regulating the flow of infusion fluid and the rotary dial 126 on the other side of the device is connected to the circuitry for controlling the interface of the device. The drop sensor is an array of IR LED 118 and photodiode 120 pairs positioned opposite to each other, with the drip chamber 114 being positioned in between the LED 118 and photodiode 120 pairs. The device 100 is clamped to the infusion system in such a way that the drops 122 falling from the infusion fluid container passes in between the line of sight of IR LED 118 and photodiode 120. In this particular embodiment, infrared emitters and transmitters are used as drop sensors whereas other means such as ultrasound means, piezoelectric means, capacitive means or any other means known in the art that can effectively function as drop sensors can be used without limiting the scope of the present disclosure.

Figure 4:
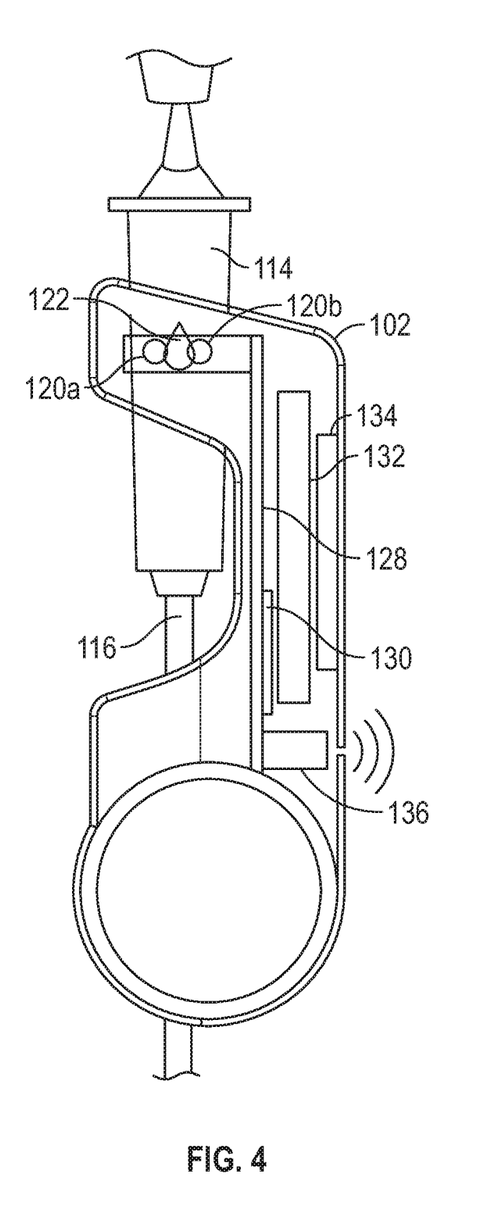
FIG. 4 is a schematic representation of a partially cutaway view of the infusion control device shown in FIG. 2. Clamping mechanism not shown for purposes of clarity.
Figure 5A:
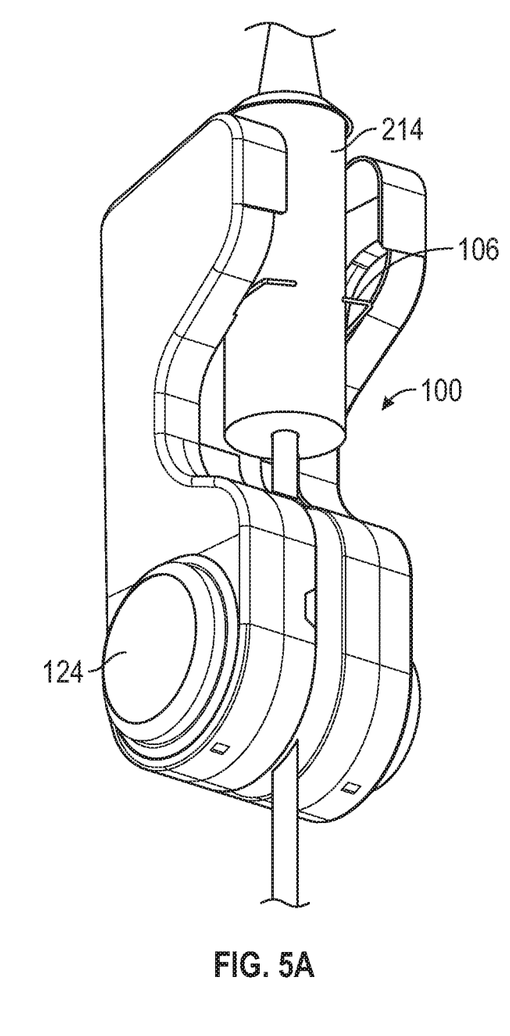
Figure 5B:
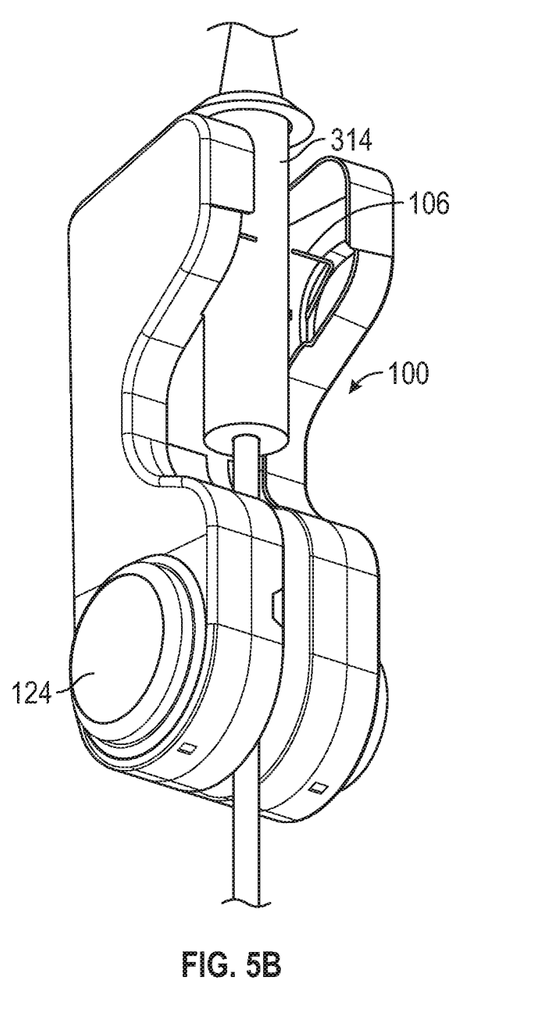
Figure 6A:
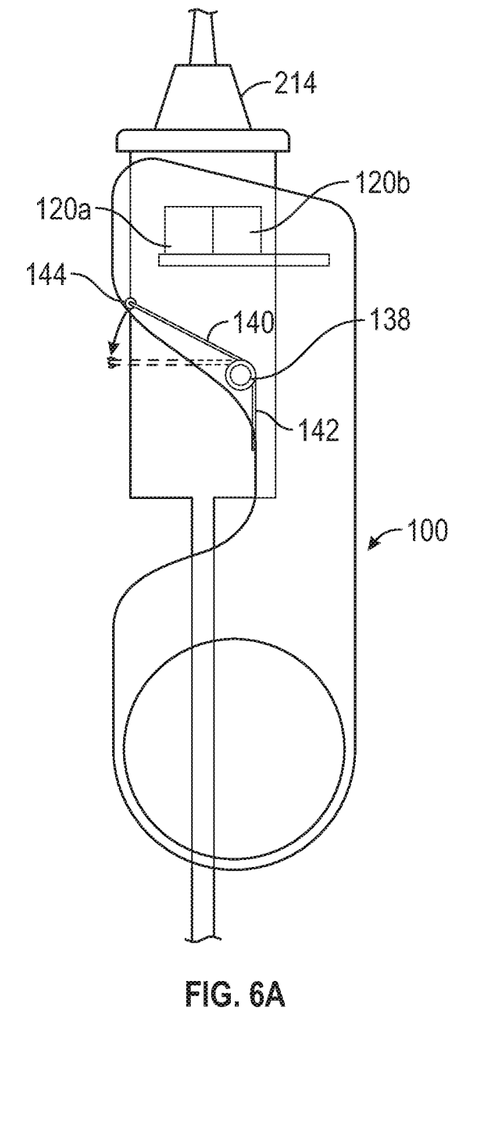
Figure 6B:
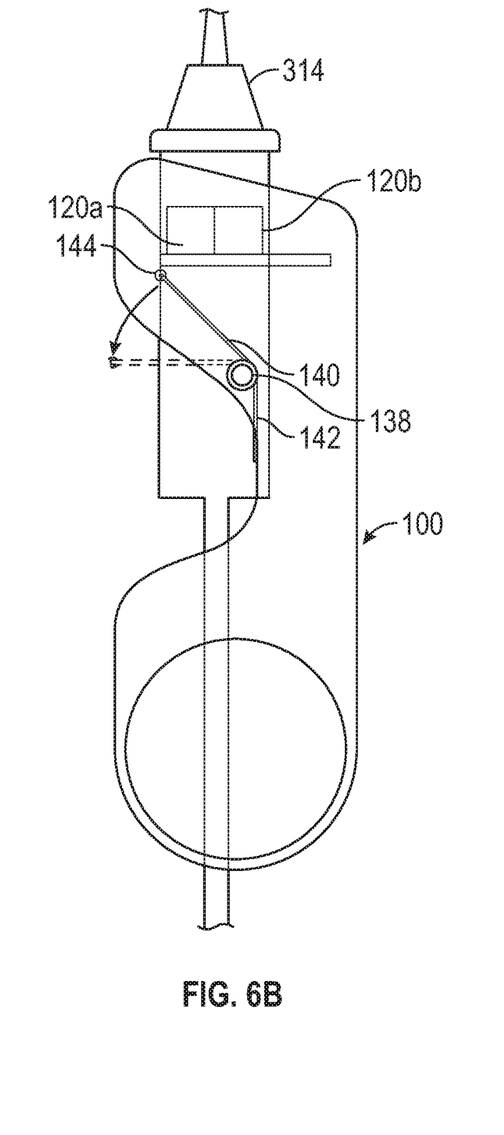

Referring specifically to FIG. 4, the photodiodes 120a and b are disposed in such a way that it always receives the light rays coming from the IR LEDs disposed in the opposite side. The drop 122 creates a dip in the intensity of light incident on photodiodes 120a and b and this is converted to electrical energy, which is amplified and fed to the interrupt pin of a Microcontroller Unit 130 (MCU) in the circuitry 128. MCU 130 calculates the time between successive drops and displays the output on a user display 134. A battery 132 is disposed within the housing 102 for powering the drop sensor and the circuits. The device also contains a buzzer alarm 136 for alerting users when there is a deviation from desired infusion parameters.

The device has an improved drop sensing mechanism and addresses the problem of optimal sensing during unwanted movements. The area of sensing is increased by providing multiple sensors adjacent to each other and the torsion-spring based clamping mechanism is devised to keep the line of fluid flow within the angle of view of the sensors. The placement of the emitters and the transmitters are aligned according to the measurements of the channel and the clamping mechanism so that drop sensing is optimal and efficient.

Figure 7A:
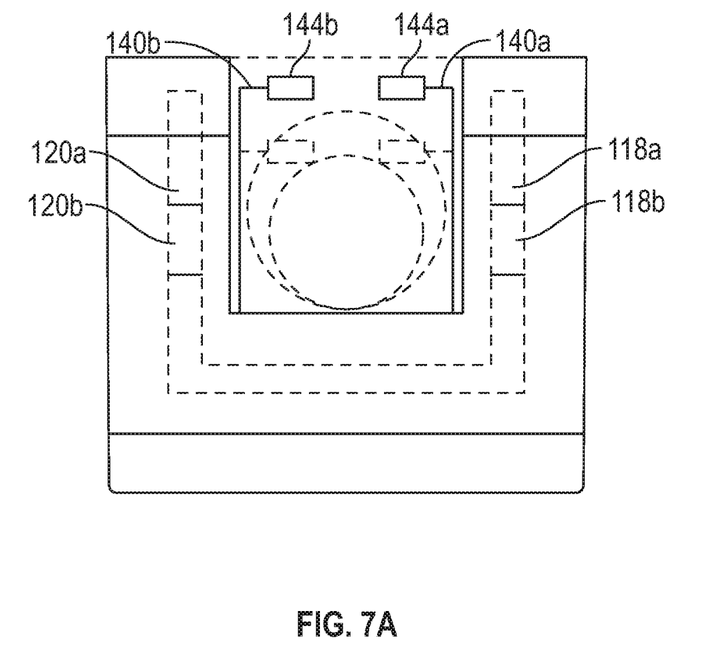
FIGS. 7A and 7B are simplistic representations of a top view and a side view of the infusion control device that depict the variation in the position of the torsion spring legs corresponding to the diameter of the drip chamber.
Figure 7B:
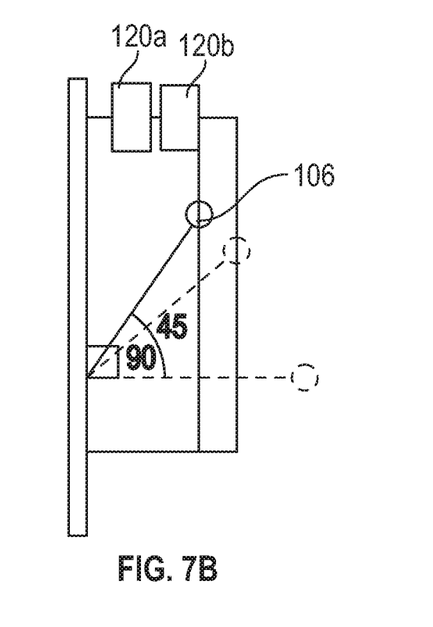
Figure 8A:
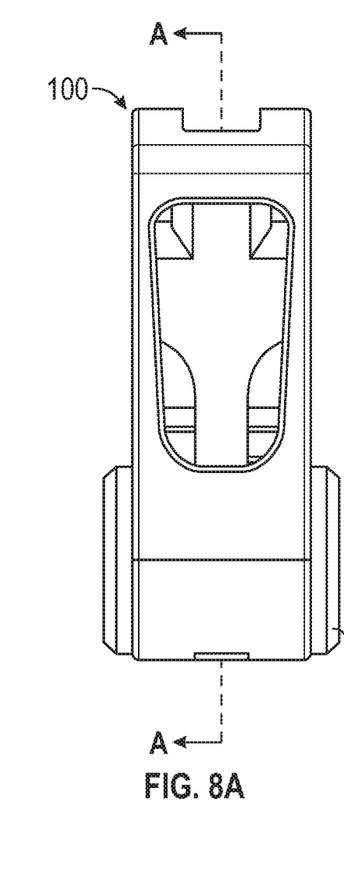
FIG. 8A is a schematic representation of a front view of the infusion control device.
Figure 8B:
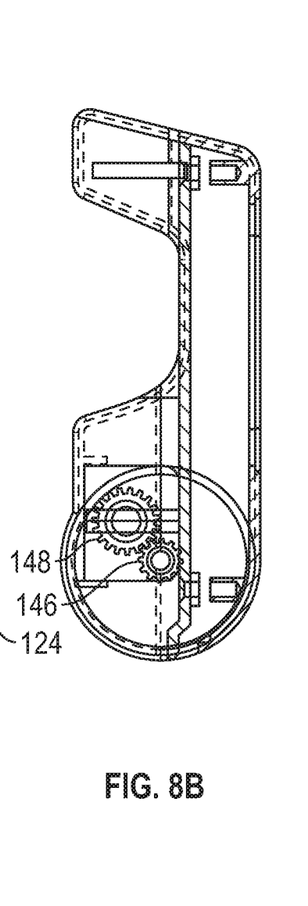
FIG. 8B is a schematic representation of a cross sectional view of the infusion control device taken along the lines A-A of FIG. 8A.
Figure 8C:
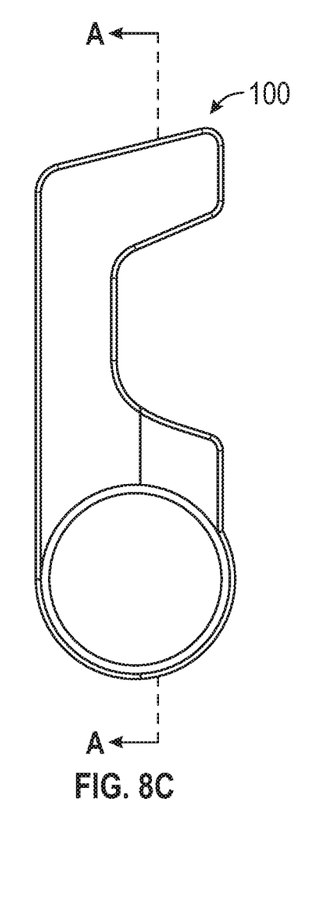
FIG. 8C is a schematic representation of a side view of the infusion control device.
Figure 8D:
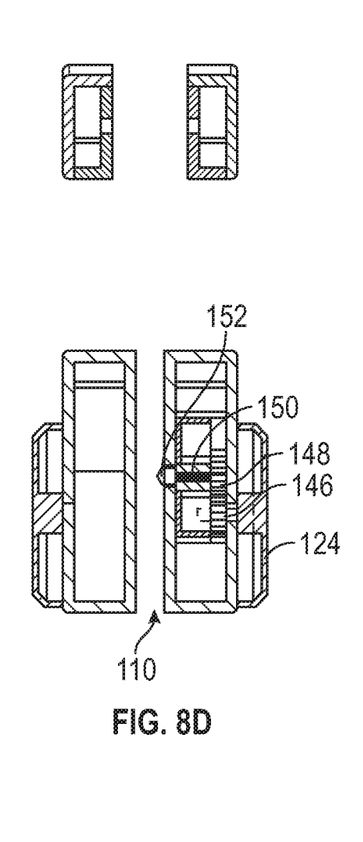
FIG. 8D is a schematic representation of a cross sectional view of the infusion control device taken along the lines A-A of FIG. 8C.

Referring specifically to FIGS. 5A-7B, the clamping mechanism comprises of two torsion springs 106 and each of the torsion spring 106 is disposed adjacent to each of the side walls of the upper portion of the channel. The spring coil 138 in the torsion spring 106 ends in two tangentially extending legs, with the first leg 140 extending forwards and bent at about right angles to engage and hold the drip chamber 214 or 314. The second leg 142 extends downwards and away from the spring coil 138 and the first leg 140. In this particular embodiment, the first leg 140 of the torsion spring is 18 mm in length and has a protective cap 144 at one end. When the drip chamber 214/314 is inserted into the upper portion of the channel, the torsion spring 106 moves towards a direction that is perpendicular to the vertical axis of the device 100. FIGS. 5A to 6B show how the torsion spring 106 angle gets auto-aligned when different sized drip chambers 214, 314 are accommodated within the channel. FIGS. 7A and 7B show how the area in the upper portion of the channel is adjusted to fit drip chambers of different sizes by moving the torsion spring legs 140. In preferred embodiments, the devices are configured to accommodate drip chambers ranging from 13 mm to 20 mm in diameter. The device has two IR emitters (LED) 118a and b on one side and two IR transmitters (Photodiode) 120a and b on the opposite side with the drip chamber being configured to be positioned in between. When the device is not attached to an infusion system, the first leg 140 lies at an angle of about less than 45 degrees with the horizontal axis of the device. As a larger drip chamber is used, the torsion spring moves downwards from 45 to about 90 degrees depending upon the diameter thus increasing the area available for accommodating the drip chamber. The force vectors perpendicular to the inner wall from the torsion spring 106 holds it towards the drip chamber. When fully retracted, the clamping mechanism can hold a drip chamber with diameter that is almost equal to the length of the spring leg. The dimensions of the housing, the channel and the torsion spring can be varied to accommodate a drip chamber of any desired dimensions without limiting the scope of the present disclosure. With reference to the dimensions of the torsion spring, the length of the legs, the bent configuration of the first leg and the angle between the spring coil and the legs can be varied according to the dimensions of the drip chamber without limiting the scope of the present disclosure. The torsion springs can be one or more in number and can be positioned anywhere in any orientation in the upper portion of the channel for efficiently engaging and holding the drip chamber without limiting the scope of the present disclosure.

Referring to FIGS. 8A to 9C, they depict manual flow regulation mechanism for the infusion devices. The mechanism comprises of a mechanical dial 124, a small first gear 146 with a first axle 154 with one end of the first axle 154 being connected with the dial 124. The small, first gear 146 is enmeshed with a big, second gear 148 having a hollow axle 158. A drivable pinching element comprising a threaded shaft 150 with a stopper 152 at one end is substantially housed within the hollow axle 158 and is configured for sliding into the channel and compressing the infusion tubing thereby regulating the flow of the infusion fluid through the infusion tubing. When the dial 124 is driven manually, the first axle 154 rotates thereby causing rotation of the first and the second gears 146, 148 leading to the linear (back and forth) reciprocating movement of the pinching element, whereby the stopper 152 compresses the infusion tubing. When the dial 124 is rotated clockwise, it rotates the first small gear 146 in the same direction and the second big gear 148 in the counter clockwise direction. This rotates the grooved hollow axle 158 of the second big gear 148 counter clockwise and the threaded shaft 150 of the pinching element housed within it clockwise. Since back-and-forth movements of the gear and its axle are arrested, the threaded shaft 150 moves forward through a hole in the housing to compress the infusion tubing thereby regulating the flow of the infusion fluid. Here, the rate of constriction depends on the pitch of the guide screw and thus can be uniformly controlled throughout the constriction process.

In this embodiment, the first gear 146 couples with the second gear 148 with a gear ratio 1.5. The hollow axle 158 of the second gear 148 is threaded with about 3 mm diameter. The threaded shaft 150 is about 3 mm in diameter and has a pitch of about 0.75 corresponding to the inner dimensions of the hollow axle 158. The stopper moves in between two ribs across the channel in which the infusion tubing is placed and constricts the tube against the inner wall.

The pitch of the screw and the gear ratio were selected in such a way that the rate of movement suffice to provide good resolution in setting the rate. In preferred embodiments, the resolution is about ±2 from the set drop rate for drop rates ranging from about 5 to 250 drops per minute. In a particular embodiment, one rotation of the dial produces a lateral movement of 0.5 mm in the stopper.

Figure 9A:
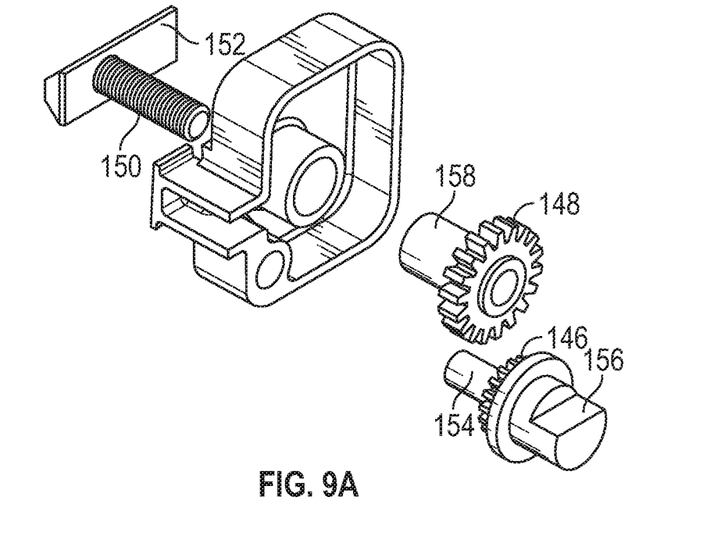
FIG. 9A is an exploded view of the mechanical flow regulation mechanism for infusion control devices, in accordance with a non limiting exemplary embodiment of the present disclosure.
Figure 9B:
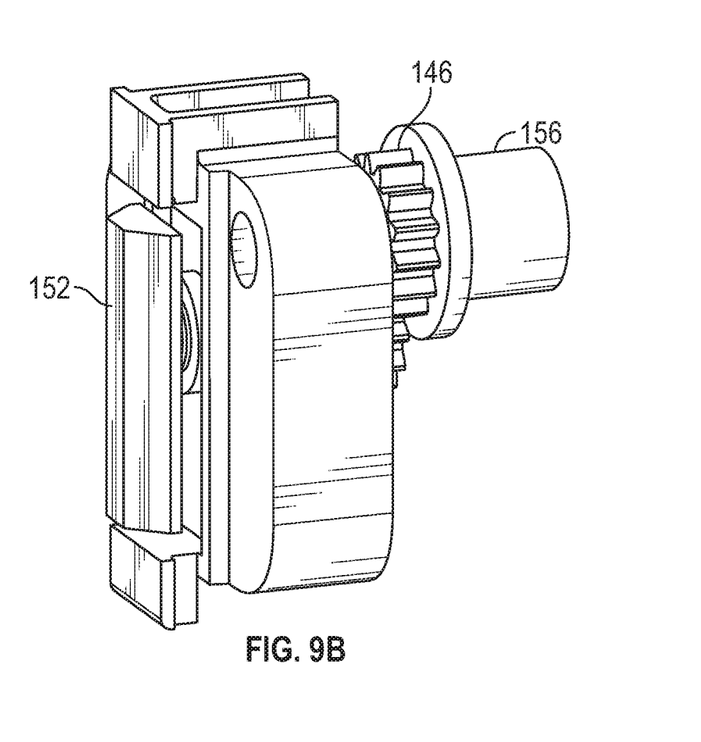
FIGS. 9B and 9C are isometric views of the mechanical flow regulation mechanism with the pincher element being retracted and extended respectively.
Figure 9C:
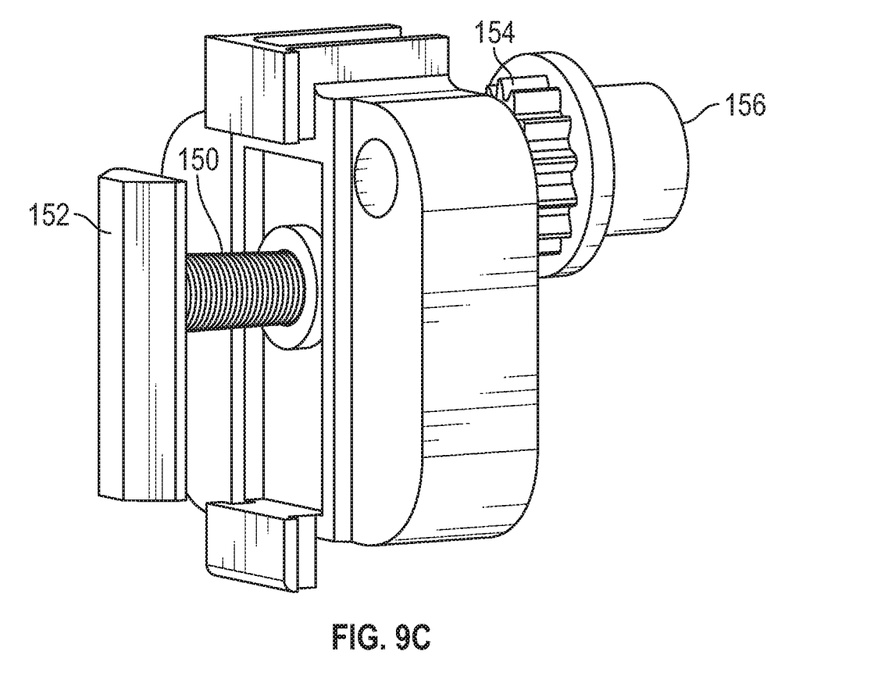
Figure 10A:
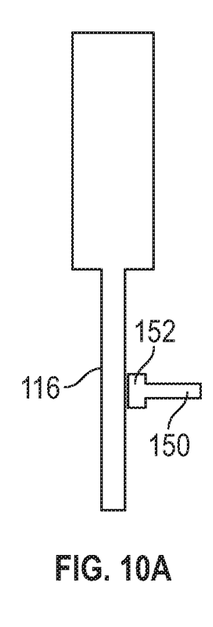
FIG. 10A-10C are simplistic representations of three pinching elements with different shaped stopper heads.
Figures 10B, 10C:
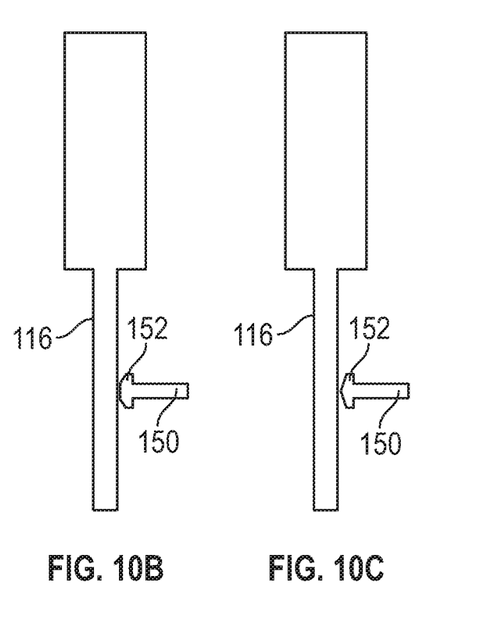

The flow regulating mechanism of the disclosed device is configured in such a manner to minimise the effects of creep and hysteresis. Effect of creep increases with the static pressure applied on the walls of tubing. The static pressure applied is proportional to the area of contact of the tube and stopper head. Referring to FIGS. 10A-10C, creep effect would be highest for the stopper profile 152 depicted in 10C and lowest for the stopper profile 152 depicted in 10A. But the stopper heads 152 depicted in FIG. 10A would require more force as compared with other stoppers for achieving the desired flow rate. The stopper head 152 profile depicted in FIG. 9B is optimal when compared with other stopper head profiles in that it does not require too much force for regulating flow nor it produce too much creep effect. In a particular embodiment, the stopper head has a flat surface of 2 mm which creates adequate movement, reduced creep effect and good resolution while setting the rate.

Other factors that affect the precision of drop rate regulation are the rate of movement of the stopper and the area of contact between the tube and the stopper head. Controlling the fluid flow by each and every drop manually requires a very slow movement of the stopper towards the tube and an optimal surface area of contact. The stopper head along with the gear mechanism of the present device is configured considering the above factors. The lateral movement of the stopper head towards the tube is made fine with the gears, connected to the manual dial. As a result the user can get a fine control for flow regulation of the infusion fluid. The area of constriction is designed considering the effect of creep and fluid flow control resolution. The stopper head profile can be configured to reduce the effect of creep to a lower level and also to make the control fine.

Figure 11:
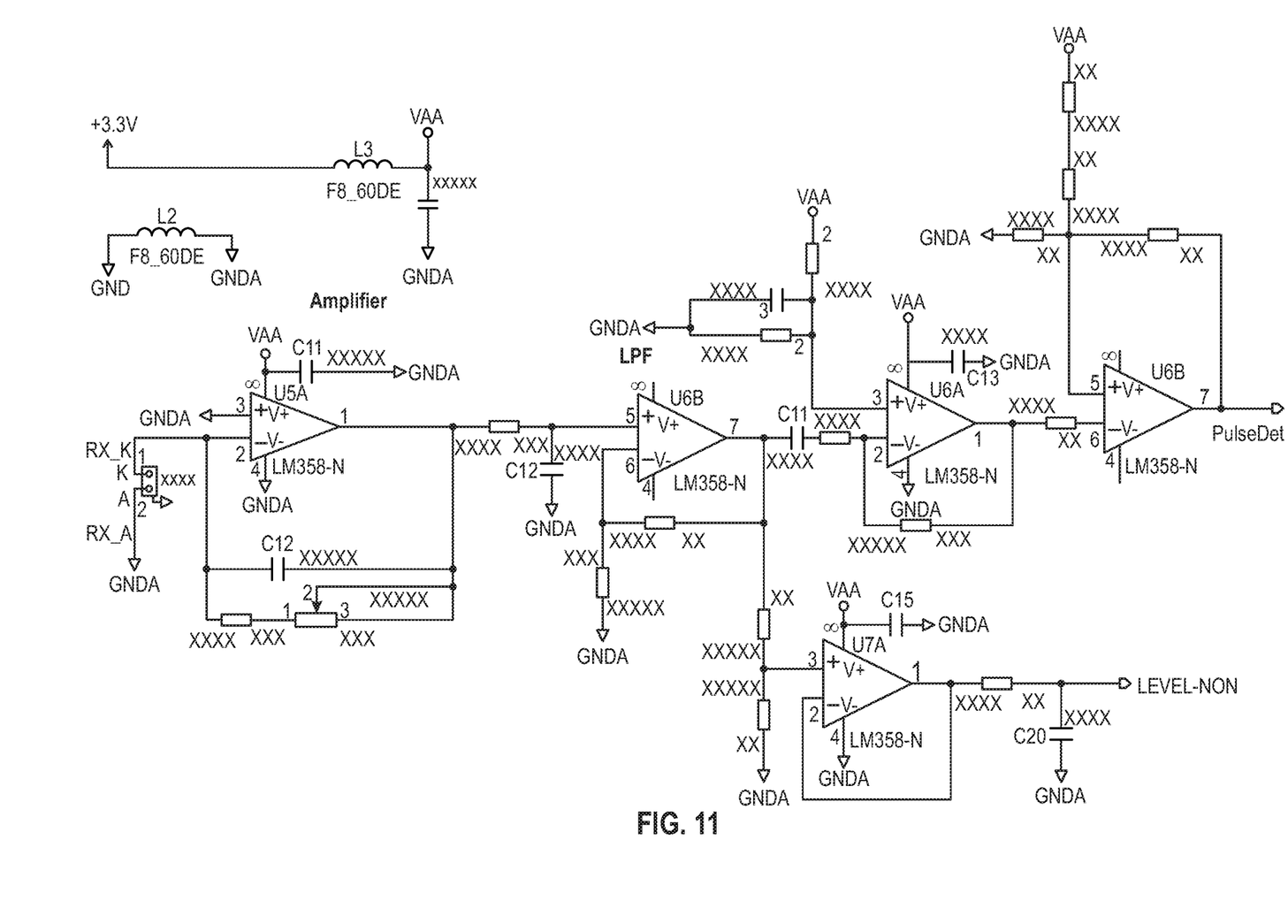
FIG. 11 is a schematic representation of a drop rate detecting circuit that is connected with a drop sensor, in accordance with a non limiting exemplary embodiment of the present disclosure.

Referring to FIG. 11, it depicts a filter circuit connected with the drop sensor for detecting real time drop rate. The filter circuit is implemented in such a way that it generally detects a dip in IR emission due only to the drops passing through the sensing area and no other obstructions, such as hand movements, in the field of view of the IR LED-Photodiode will be detected as a drop. The time of drop fall is found to be 732 milliseconds. The filter and pulse detector detects only the drops that causes ~732 ms interruption and discard any other inferences caused by human interaction or any other external factors. A digital resistor is also included so that the circuit can auto calibrate itself with the help of software to detect drops in different lighting conditions.

The circuits depicted herein comprises of a current amplifier, a low pass filter, a level monitor and a pulse detector. The current amplifier amplifies low signals received from the photodiode and the amplification levels can be varied by using a potentiometer. The low pass filter filters out low frequency noises during the detection. The level monitor is used for setting a detection threshold based on ambient light conditions. The pulse detector detects the pulses from the low pass filter and amplifies the output when then passes the signal to the microcontroller.

The drop sensor detects a dip in the incoming light which includes not only the light from the IR emitter but also the ambient light. In a particular embodiment, the software based automatic calibration code in the device adjusts the light emitted by the emitter according to the lighting conditions so that detection efficiency remains the same at different lighting conditions. The sensor detects light beyond certain threshold and it sends a signal to microcontroller. IR emitter is pulsed with a pwm signal to control the intensity of light emitted from a larger value to smaller values and the sensor threshold point is detected. Once the intensity for IR led to keep the incident light at threshold value for the sensor is detected, IR is pulsed at the same value so that the incidence of a drop causes fall from the threshold and detection trigger.

The following is an example for setting a detection threshold, wherein IR is pulsed at 38 KHz max input voltage 3.3V. Intensity of the IR can be varied according to the lighting conditions by changing input voltage. Lighting condition is monitored by using the photodiode. The level monitor that is connected with the photodiode detects the lighting condition. The output of the level monitor gives an output from 0V-1V or 0-1024 (adc value) steps according to the lighting condition. The filter circuit is designed in such a way that, the drop detection only happens when the level monitor output is maintained around 0.5v or adc value 512. When surrounding light is low, Level Monitor output will be less than 0.5V or 512 adc value. Software detects the level monitor value and intensity of the IR led is increased by 5 steps gradually till the level monitor value is maintained to 0.5V. When surrounding light is high, Level Monitor output will be greater than 0.5V or 512 adc value. Software detects the level monitor value and intensity of the IR is decreased by 5 steps gradually till the level monitor value is maintained to 0.5V.

Drop per minute reading displayed on the device is shown by calculating the time between two drops. But at higher rates (drops per minute>60) the rate read out suffers from noise. In existing infusion monitors filters are implemented to control this fluctuations in rate so that the monitors always show a constant read out even at higher rates. A moving average of the inputs rate for windows of 10 reading might be used to show a constant rate. If the user constricts the tube and bring down the drop rate say from 100 to 20, the device readout may not display the final rate 20 at instance as it takes more time for drops at a rate of 20 to pass so as to make the moving average come down to 20. This takes more time at lower rates and causes inconvenience in setting the rate. The device disclosed herein includes a selective filtering module, wherein the device gives a real time drop rate without a moving average at lower drop rates but gives a moving average only at higher drop rates say at rates of more than about 60 drops per minute.

Although the present disclosure has been described in terms of certain preferred embodiments and illustrations thereof, other embodiments and modifications to preferred embodiments may be possible that are within the principles and spirit of the invention. The above descriptions and figures are therefore to be regarded as illustrative and not restrictive.

Thus the scope of the present disclosure is defined by the appended claims and includes both combinations and sub combinations of the various features described herein above as well as variations and modifications thereof, which would occur to persons skilled in the art upon reading the foregoing description.

We claim:

1. An infusion control device for monitoring and setting the flow of an infusion fluid in an infusion system comprising:
   a) a housing defining a channel there through, an upper portion of the channel thereof being configured for accommodating at least a part of a drip chamber and a lower portion of the channel thereof being configured for accommodating at least a part of an infusion tubing;
   b) a clamping mechanism comprising at least one of a torsion spring, the clamping mechanism thereof being configured for engaging and holding the drip chamber within the upper portion and to be adjusted according to the diameter of the drip chamber;
   c) a drop sensor for detecting the drops falling through the drip chamber, the sensor thereof being disposed in the upper portion adjacent to the drip chamber;
   d) circuits being coupled with the drop sensor and disposed substantially within the housing, the circuits thereof being configured for processing the information received from the sensor for detecting real time drop rate of the infusion fluid;

e) a manual flow regulation mechanism disposed substantially within the housing and comprising a drivable pinching element for sliding into the channel and compressing the infusion tubing thereby regulating the flow of the infusion fluid through the infusion tubing; and f) a power source disposed within the housing and configured for powering the drop sensor and the circuits.

2. The device of claim 1, wherein the clamping mechanism comprises of two torsion springs, each torsion spring thereof being disposed adjacent to each of the side walls of the upper portion, each of the spring coil thereof ending in a tangentially extending first leg, each of the first leg thereof being bent and configured for engaging and holding the drip chamber.

3. The device claim 1, wherein the drop sensor comprises of at least one of an IR emitter and at least one of an IR receiver, the IR emitter and the IR receiver thereof being disposed opposite to each other with the drip chamber being positioned in between, the sensor thereof being configured for optimal sensing of drops from different sized drip chambers.

4. The device of claim 1, wherein the circuits comprise of an amplifier for amplifying the signal from the drop sensor, a low pass filter for filtering out low frequency noises and a level monitor for setting a detection threshold based on ambient light conditions, the circuit thereof being generally configured for detecting a dip in IR emission only due to the infusion drops and not due to any other obstructions.

5. The device of claim 4, wherein the circuits are connected with a display unit for displaying the real time drop rate of the infusion fluid.

6. The device of claim 1, wherein the regulation mechanism further comprises of a dial disposed over the housing; a first gear with a first axle, one end of the first axle thereof being connected with the dial, a second gear with a hollow axle, the second gear thereof being enmeshed with the first gear, the pinching element being substantially housed within the hollow axle, the pinching element thereof comprising a threaded shaft with a stopper at one end, whereby, when the dial is driven manually, the first axle rotates thereby causing rotation of the first and the second gears leading to the linear movement of the pinching element, whereby the stopper compresses the infusion tubing.

7. The device of claim 6, wherein the regulation mechanism is configured for minimising the effect of creep and hysteresis.

8. The device of claim 1, comprising a selective filtering module, wherein the device gives a real time drop rate without a moving average at lower drop rates and gives a moving average at higher drop rates.

9. The device of claim 1, comprising an alarm substantially disposed within the housing for alerting users when there is a deviation from desired infusion parameters.

10. A manual infusion fluid regulation mechanism for infusion devices comprising a rotary drive configured for being manually driven, a first gear with a first axle, one end of the first axle thereof being connected with the drive, a second gear with a hollow axle, the second gear thereof being enmeshed with the first gear, a drivable pinching element being substantially housed within the hollow axle, the pinching element thereof comprising a threaded shaft with a stopper at one end for sliding into a channel and compressing the infusion tubing thereby regulating the flow of the infusion fluid through the infusion tubing, whereby, when the rotary drive is driven manually, the first axle rotates thereby causing rotation of the first and the second gears leading to the linear movement of the pinching element, whereby the stopper compresses the infusion tubing.

11. The regulation mechanism of claim 10, being configured for minimising the effect of creep and hysteresis.

* * * * *